United States Patent [19]

Rosengard et al.

[11] Patent Number: 5,843,778

[45] Date of Patent: Dec. 1, 1998

[54] USE OF CHIMERIC VACCINIA VIRUS COMPLEMENT CONTROL PROTEINS TO INHIBIT COMPLEMENT

[75] Inventors: Ariella M. Rosengard, Gladwyne, Pa.; Joseph M. Ahearn, Jr., Baltimore, Md.; Alfred P. Sanfilippo, Baltimore, Md.; William M. Baldwin, III, Baltimore, Md.

[73] Assignee: The Johns Hopkins University School of Medicine, Baltimore, Md.

[21] Appl. No.: 874,978

[22] Filed: Jun. 13, 1997

[51] Int. Cl.[6] .......................... C12P 21/00; C12N 15/39; C12N 5/10; C07H 21/04

[52] U.S. Cl. ................... 435/325; 435/320.1; 435/69.7; 435/172.3; 536/23.4; 536/23.72

[58] Field of Search ................................ 435/325, 320.1, 435/69.7, 172.3; 536/23.4, 23.72

[56] References Cited

U.S. PATENT DOCUMENTS 5,455,165  10/1995  Capon et al. .
5,643,770   7/1997  Mason et al. ........................ 435/172.3

OTHER PUBLICATIONS

Miller et al. Virology. 229:126–133, Mar. 3, 1997.

McKenzie et al. "Regulation of Complement Activity by Vaccinia Virus Complement–Control Protein", *The Journal of Infectious Diseases,* 1992, vol. 166, pp. 1245–1250.

Kroshus et al., "Complement Inhibition with an Anti–C5 Monoclonal Antibody Prevents Acute Cardiac Tissue Injury in an Ex Vivo Model of Pig–To–Human Xenotransplantation," *Transplantation,* Dec. 15, 1995, vol. 60, pp. 1194–1202.

Heckl–Ostreicher et al., "Functional Activity of the Membrane–Associated Complement Inhibitor CD59 in a Pig–To–Human in vitro Model for Hyperacute Xenograft Rejection", *Clin. Exp. Immunol.,* 1995, vol. 102, pp. 589–595.

White et al, "Production of Pigs Transgenic for Human DAF to Overcome Complement–Mediated Hyperacute Xenograft Rejection in Man," *Res. Immunol.,* Feb. 1996, vol. 147, No. 2, pp. 88–94.

*Primary Examiner*—David Saunders
*Assistant Examiner*—F. Pierre VanderVegt
*Attorney, Agent, or Firm*—Fish & Richardson P.C.

[57] ABSTRACT

Disclosed are chimeric proteins that are useful for inhibiting complement. The chimeric protein termed VCPFc is a fusion protein in which (i) an immunoglobulin Fc region is fused to (ii) a polypeptide that comprises a portion of a vaccinia virus complement control protein which binds complement components C4b and C3b, but not iC3b rosettes. This protein can be use in xenograft transplantation methods (e.g., by treating the donor mammal or organ) and in methods for treating complement-mediated disorders (e.g., inflammation) generally. In a second chimeric protein, a transmembrane anchoring domain is fused to a polypeptide that comprises a portion of a vaccinia virus complement control protein which binds complement components C4b and C3b, but not iC3b rosettes. The transmembrane anchoring domain can be, for example, short consensus regions 3 through 15 of human complement receptor 2 protein. Expression of the transmembrane-anchored fusion protein in a transgenic animal provides a well-suited organ donor for xenograft transplantation.

7 Claims, 10 Drawing Sheets

USE OF CHIMERIC VACCINIA VIRUS COMPLEMENT CONTROL PROTEINS TO INHIBIT COMPLEMENT

STATEMENT AS TO FEDERALLY SPONSORED RESEARCH

This invention was made, at least in part, with funds from the Federal Government awarded through the National Institutes of Health (Grant HLB31331).

CROSS-REFERENCE TO RELATED APPLICATIONS

This application claims priority under 35 U.S.C. § 119 from Provisional Application Ser. No. 60/019,920, filed Jun. 14, 1996, and Provisional Application Ser. No. 60/019,801, filed Jun. 14, 1996.

1. Field of the Invention

The present invention relates generically to the field of transplantation and rejection and specifically to a method for preventing rejection by transplant recipients and in improving the function of donor organs and tissues by inhibition of complement.

2. Background of the Invention

Although the immune response is often perceived as beneficial, in certain circumstances the immune response to an antigen can actually be harmful to the animal in which the immune response occurs. Examples of situations where the immune response creates conditions where the animal is subject to serious pathologic sequelae are in such areas as graft versus host (GVH) rejection and host versus graft (HVG) rejection, and certain autoimmune diseases, such as lupus erythematosus, insulin-dependent diabetes mellitus, multiple sclerosis, myasthenia gravis, and rheumatoid arthritis.

The utilization of organs from nonhuman donors is an appealing solution to the increasing shortage of organs available for clinical transplantation. Although xenotransplantation from primate donors has been performed with limited success clinically, the use of distantly related species, such as the pig, avoids ethical dilemmas, potential virus transmission, and limited availability associated with the use of primates as xenograft (Xg) donors. However, the use of organs from distantly related species for xenotransplantation has been hampered by the occurrence of hyperacute rejection (HAR), a process that leads to irreversible Xg damage and loss within minutes to hours of transplantation. HAR is thought to be mediated by the binding of naturally occurring xenoreactive antibodies to the endothelium of the Xg, in particular, donor vascular endothelial cells, with subsequent activation of the classical pathway of complement (C). It has been shown that a predominate specificity of these antibodies is to the oligosaccharide moiety galactose ($\alpha$1–3)galactose for primate recipients. Alternative C pathway activation also contributes to HAR in some species combinations. The complement cascade is activated following the binding of xenoreactive antibodies to donor tissue. This cascade leads to endothelial activation, thrombosis, intravascular coagulation, edema, and eventually loss of function of the transplanted organ. However, if xenoreactive natural antibodies are eliminated, the presence of complements is still adequate to mediate a rejection event, presumably via the alternative pathway.

Complement-mediated cell lysis also plays a role in allograft rejection, and has therefore presented a hurdle in methods of allograft transplantation. Thus, complement-mediated tissue deterioration can cause dysfunction of donor organs and tissues both from human and non-human sources. In addition, complement activation causes the deterioration of blood products, such as platelets. Thus, the length of time that blood can be stored (e.g., for transfusions) is diminished by the activity of complement.

Humans and microorganisms express complement inhibitors (CIs), which serve to inhibit complement-mediated attacks. CIs contain short consensus repeats (SCRs), which are 60–70 amino acid-long regions. The number of SCRs varies among CIs. For example, the human CI Complement Receptor 1 (CR1) has 30 SCRs, while the human CI Decay Accelerating Factor (DAF) has 4 SCRs. The binding specificity of the various CIs for the various complement factors also varies. For example, Complement Receptor 1 (CR1) in humans binds C3b, C3bi, and C4b, and functions via two mechanisms: Factor I cofactor activity and convertase decay acceleration. Another human CI, Decay Accelerating Factor (DAF) binds C3b and C4b, but only has convertase decay accelerating activity. Membrane Cofactor Protein (MCP), a different human CI binds C3b and C4b, but only has Factor I cofactor activity.

SUMMARY OF THE INVENTION

The invention provides a fusion protein that can be used to inhibit graft rejection and complement-mediated disorders generally. In particular, the invention provides a fusion protein in which (i) an immunoglobulin Fc region (e.g., IgG Fc) is fused to (ii) a polypeptide that includes a portion of a vaccinia virus complement control protein (VCP) that binds complement components C4b and C3b, but not iC3b rosettes. A preferred fusion protein includes short consensus regions 1 through 4 of VCP as the polypeptide that is fused to an immunoglobulin Fc region. The Fc portion of VCPFc confers stability to the fusion protein in vivo, thereby increasing the circulating half-life of the fusion protein, relative to that of VCP alone.

The fusion protein of the invention, termed VCPFc, can be used in a method of allograft or xenograft transplantation, involving administering VCPFc to a donor mammal (e.g., a pig or human) to attain therapeutic levels of VCPFc by the time an organ is removed from the donor for transplantation. If desired, upon removing the organ prior to transplantation, the donor organ (e.g., a heart) can be treated (e.g., flushed) with VCPFc in a pharmaceutically acceptable carrier. The xenograft transplantation method can also include administering an immunosuppression agent to the xenograft recipient substantially contemporaneously with the transplant, for example. The invention also includes a method for inhibiting a complement-mediated disorder in a mammal generally. The method involves administering to the mammal an inhibition effective amount of a fusion protein that includes an immunoglobulin Fc region fused to a polypeptide that includes a portion of a vaccinia virus complement control protein that binds complement components C4b and C3b, but not iC3b rosettes. The VCPFc fusion protein also can be used in a method for inhibiting complement-mediated deterioration of a blood product by adding an inhibition-effective amount of VCPFc to a blood collection or storage unit containing a blood product (e.g., whole blood or a solution containing any component(s) of blood), thereby inhibiting complement-mediated deterioration of the blood product. In particular, VCPFc is useful for inhibiting complement-mediated deterioration of a blood product that includes platelets.

In another aspect, the invention provides a transgenic mammal (e.g., a pig), the genome of which includes a gene that encodes a fusion protein that inhibits rejection of an organ transplanted from the mammal to a recipient. Specifically, the fusion protein includes (i) a transmembrane anchoring domain fused to (ii) a polypeptide that includes a portion of a vaccinia virus complement control protein that binds complement components C4b and C3b, but not iC3b rosettes. A preferred fusion protein includes (i) a polypeptide that includes the short consensus regions 3 through 15 of human complement receptor 2 protein, fused to (ii) a polypeptide that includes short consensus regions 1 through 4 of vaccinia virus complement control protein. Short consensus regions 3 through 15 of the human complement receptor 2 protein render this fusion protein membrane-bound, thus reducing concerns about clearance of the fusion protein from the circulation. Alternative methods that can be adapted to bind VCP to a cell membrane are described in U.S. Pat. No. 5,109,113, which is incorporated herein by reference. An organ(s) of this transgenic mammal can be transplanted to a recipient (e.g., a human) in a method of xenograft transplantation. Expression of the fusion protein in an organ derived from the transgenic mammal inhibits activation of complement and thereby inhibits rejection of the xenograft. If desired, an immunosuppression agent can be administered to the recipient substantially contemporaneously with the transplant.

BRIEF DESCRIPTION OF THE DRAWINGS

FIG. 1 is a map of the expression construct pRelVCP1234. The immediate early CMV promoter of CDM8 drives transcription of the insert that encodes a VCP-CR2 chimeric receptor in which SCR-1 and SCR-2 of wild type human CR2 have been replaced with SCR-1 through −4 of wild type VCP. The unique PspAI and XhoI sites were also used to insert cassettes in which one or two SCR of VCP were deleted.

FIGS. 2A–2C provide a schematic representation, recombinant protein expression levels, and C3b dimer binding-capacity of K562.wild type, K562.CR1, and six K562.VCP deletion mutants.

FIG. 3 represents a flow cytometric analysis of mouse L cells expressing recombinant proteins. L cells.wild type (FIG. 3A), L cells.RelVCP1234 (FIG. 3B) and L cells.CR1 (FIG. 3C) indirectly stained with control anti-body (thin solid line) or either HB5 anti-SCR-3 and 4 of CR2 (thick solid line) for wild type and L cell.RelVCP1234 or YZ1 anti-CR1 for wild type and L cell.CR1 (thick solid line) followed by fluorescein-conjugated goat anti-mouse Ig.

FIGS. 4A and 4B show the levels of expression after 3 (FIG. 4A) or 7 (FIG. 4B) exposures to heat inactivated rabbit complement. FIGS. 4C–4D shows the level of expression after 3 (FIG. 4C) or 7 (FIG. 4C) exposures to normal rabbit complement.

DESCRIPTION OF THE PREFERRED EMBODIMENTS

The invention involves application of a recombinant protein termed "VCPFc" in pretreating a donor and, if desired, a donor organ ex vivo before transplantation in order to prevent rejection of an allograft or xenograft (i.e., the transplanted organ(s) or tissue(s)). Although not bound by any particular mechanism, such graft rejection reactions are thought to be due to complement activation resulting from antibody binding and/or complement dysregulation. Immediately prior to transplantation, VCPFc is administered to a donor to attain therapeutic levels of VCPFc in the donor (and specifically in the donor organ) by the time the organ is removed from the donor for transplantation. Following removal of the organ, and prior to transplantation, the donor organ can be treated (e.g., flushed) with VCPFc in a pharmaceutically acceptable excipient.

Typically, the organ recipient is treated prior and/or subsequent to transplantation with an immunosuppressive agent(s) that inhibits the host's antibody and cellular immune responses to the donor organ. For example, the invention includes a method for treating pig heart donors for transplantation of the hearts to human recipients. An illustrative treatment protocol follows: beginning one week prior to the transplantation, cyclophosphamide is administered to the recipient in order to reduce the potential for evoking an antibody response to the transplant. An immunosuppressive dose of cyclosporine or FK506 may be started shortly (e.g., 1–3 days) before transplantation to enhance graft acceptance. Immediately prior to transplantation, the donor is dosed with VCPFc to attain therapeutic levels by the time of donor organ removal. Upon removal prior to transplantation, the donor organ is flushed with a solution containing VCPFc. Following transplantation by standard surgical techniques, the patient is maintained on routine immunosuppression using cyclosporine or FK506, cyclophosphamide and steroids plus VCPFc. Based on clinical signs and symptoms related to immune responsiveness, various of the immunosuppressants are reduced in dosage.

The immunosuppressive agent used according to the method of the invention is an agent such as Cyclosporine A (CsA), however other agents that cause immune suppression, such as rapamycin, desoxyspergualine, and FK506 or functional equivalents of these compounds, can also be utilized. CsA is preferably administered by injection at an immunosuppressive dose. The duration of CsA treatment may range from about 2 to about 20 days.

In a second aspect, the invention provides a method for inhibiting a complement-mediated disorder in a mammal, i.e., any condition in which complement activity is undesirably high. Examples of complement-mediated disorders include, but are not limited to, inflammation (including neurological inflammation), spinal cord injuries, arthritis, ischemia-induced reperfusion injuries, glomerulonephritis, encephalomyelitis, and burns. An inhibition effective amount of VCPFc is an amount that inhibits at least 20%, preferably 50%, and most preferably 90% of complement activity. If desired, an inhibition effective amount of VCPFc can be identified as an amount that ameliorates a sign(s) or symptom(s) of a complement-mediated disorder.

Although a preferred embodiment of the invention involves transplantation of a pig heart into a human, it is understood that any organ can be transplanted. For example, other transplantable organs include cornea and kidney. Further, while the pig is the preferred donor, other donors may also be used. The human is the preferred recipient.

As used herein, "substantially contemporaneously" refers to the time at which the immunosuppressant is administered to the recipient in relation to the time at which the organ is transplanted. For example, a heart transplant recipient may receive CsA for a short time prior to and immediately following the transplant for about 10–16 days, preferably about 14 days. In general, where transplant grafts are involved, the immunosuppressive agent can be administered from about 1 day to about 90 days before the transplant and until about 7 days to about 90 days after the transplant. Preferably, the immunosuppressive agent is administered from about 7 days to about 28 days before until about 7 days to about 28 days after.

If desired, complement activity in the donor can be measured in the donor prior to transplantation of the organ. A "pre-assay", pre-existing, complement activity is determined by $CH_{50}$, a standard procedure known to those of skill in the art (see for Example, Manual Clinical Immunology). Preferably, the fusion protein is expressed at a level sufficient to reduce complement activity to about 10% of the normal complement activity level in the donor.

The invention also provides a transgenic mammal that is useful as a donor in organ transplantation methods. The transgenic mammal of the invention, or an ancestor of the mammal, is genetically engineered to encode a fusion protein that includes (i) a membrane anchoring domain (e.g., the short consensus regions 3 through 15 of human complement receptor 2 protein) fused to (ii) the short consensus regions 1 through 4 of vaccinia virus complement control protein. Conventional methods for producing transgenic mammals can be used to express a gene encoding the fusion protein as a transgene in a mammal (see, e.g., Elizabeth Hogan et al., *Manipulation of the Mouse Embryo*, 1994, Cold Spring Harbor Press, Cold Spring Harbor, N.Y.). The promoter of the construct could be the same as in the PiCR2 plasmid, i.e., CMV, or a different one.

In all of the various aspects of the invention, the recipient can be treated prior or subsequent to transplantation with an immunosuppressive agent(s) that inhibits the host antibody and cellular immune responses to the donor organ.

The following examples are intended to illustrate, but not limit the invention. While they are typical of those that can be used, other procedures known to those skilled in the art may alternatively be used.

EXAMPLES

These examples employ a panel of fusion proteins having various portions of VCP fused to the transmembrane domain of CR2 (SCRs 3–15). These examples also employ a fusion protein, VCPFc, which has VCP fused to the Fc portion of an immunoglobulin. These proteins were produced and characterized as follows.

Materials and Methods

Isolation of Vaccinia Virus Complement Control Gene: The full length VCP gene was cloned by PCR-based approach using DNA from epithelial cells infected by wild type Vaccinia virus (available from the ATCC).

Creation of Expression Vectors. The CDM8 expression vector with the 4 SCR of VCP replacing SCR-1 and −2 of CR2 was called RelVCP1234. It was prepared as follows: πCR2 was ingested with PspAI and XhoI to remove SCR-1 and −2 of CR2 which were replaced by VCP. To prepare the VCP cDNA for ligation into the plasmid, site directed mutagenesis was used to destroy an internal XhoI restriction site (317–322). A silent T to A transversion was incorporated into the third position of a proline codon at position 318. This was accomplished using oligonucleotides A-XhoI and B-XhoI. Oligonucleotides PspAISCR1b and XhoISCR4 were used at the 5' and 3' ends, respectively to create the PspAI and XhoI sites. A triple ligation using ClaI (present near the mutated XhoI site) combined the 2 parts of VCP and inserted them into πCR2.

The five deletion mutants (RelVCP12, RelVCP23, RelVCP34, RelVCP123, and RelVCP234) were made in a similar fashion using oligonucleotides that created a PspAI site at the 5' end and a XhoI site at the 3' end and flanked the SCRs to be inserted. For RelVCPI2, oligonucleotides PspAISCR1b and XhoISCR2 were used. For RelVCP23, oligonucleotides PspAISCR2 and XhoISCR3 were used. For RelVCP34, oligonucleotides PspAISCR3 and XhoISCR4 were used. For RelVCP123, oligonucleotides PspAISCR1b and XhoISCR3 were used. For RelVCP234, oligonucleotides PspAISCR2 and XhoISCR4 were used. In RelVCP23 and RelVCP234, the internal XhoI site was reinserted because the primers were taken from the VCP cDNA sequence. The reinsertion of XhoI site resulted in no change in the amino acid sequence of the protein. All of the chimeras were sequenced. πABCD is the plasmid encoding the human CR1 protein.

Human anti-C3d, -C4d, and -iC3b (Quidel, San Diego, Calif.) are mouse anti-human MAb. Fluorescein (DTAF)-conjugated goat anti-mouse F(ab')2 anti-mouse IgG (Jackson Immuno Research Laboratories, West Grove, Pa.) and fluorescein-conjugated goat anti-human C3 (Organon Teknick Corp., Durham, N.C.) were used as secondary antibodies. Anti-L cell/NIH3T3 antiserum was prepared by injecting a mixture of murine L cells and NIH/3T3 cells (ATCC CRL 1658) into healthy R1 rats. Blood was collected at approximately days 10 post-injection. The serum was heat inactivated, aliquoted and fresh frozen.

Flow Cytometry: Specific protein expression was confirmed by flow cytometry. Adherent L cells were removed from culture dishes using PE buffer (PBS with 0.5 mM EDTA), washed in FACS buffer (2% BCS 0.01% NaAzide, 10 mM Hepes in PBS) and resuspended with primary antibody at 1 $\mu$/ml or ligand for 30 minutes on ice. Cells Oligonucleotides used to prepare constructs

| Name | 5'-3' sequence |
|---|---|
| PspA1SCR1b | GCACCCGGGTCCTCGGGATTTCTTGCTGTACTAATTCCGTCACGA |
| XhoISCR2 | CCGCTCGAGTTTAACAGATTCACAAATAGG |
| PspAISCR2 | GCACCGGGGTCCTCGGGATTTCTTGCCCATCGCCTCGAGATATC |
| PspAISCR3 | GCACCCGGGGTCCTCGGGATTTCTTGCCAATCCCCTCCATCTATA |
| ShoISCR4 | CCGCTCGAGGCGTACACATTTGGAAGTTC |
| A-XhoI | ATTATCGATATCTCGTGGCGATGGGCA |
| B-XhoI | CCATCGCCACGAGATATCGATAATGGC |
| PspAISCR1 | CCCCCCGGGTGCTGTACTATTCCGTCACGA |
| B-XhoISCR4 | CCGCTCGAGGCGTACACATTTTGGAAGTTC |

Tissue Culture: L-M(TK-) cells (L cells) (American Type Culture Collection, Rockville, Md., CCL 1.3) were maintained in complete DMEM (supplemented with L-glucose at 4500 mg/L, 10% bovine calf serum (BCS) (Life Technologies) or fetal bovine serum (HyClone Laboratories, Logan, Utah) and 2mM glutamine (Life Technologies) and penicillin (100 $\mu$/ml) and streptomycin (100 $\mu$g/ml) (P/S) (Life Technologies)) (Life Technologies, Gaithersberg, Md.). L cells were cotransfected with pSV.neo (2 $\mu$g) and piABCD [encoding CR1 (Klickstein et al., 1988, J. Exp. Med 168: 1699–1717)] or a VCP mutant (pRelVCP1234, pRelVCP12, pRelVCP23, pReIVCP34, pRelVCP123, or pRelVCP234) at 18 $\mu$g/100mm plate (30–40% confluent dish) using the Calcium Phosphate Transfection System (Life Technologies) per the manufacturer's directions. Stable lines were maintained in 400 $\mu$/ml of G418 (Life Technologies). G418-resistant cells expressing high levels of HB5 epitope for VCP mutants and high levels of CR-1 specific epitope, YZ-1, for CR1 expressing cells were selected using flow cytometry.

K562 cells (ATCC CCL 243) were grown in complete RPMI and supplemented as above (Life Technologies). Plasmids were cotransfected with plasmid P141 into K562 cells through LIPOFECTIN (Life Technologies) as described previously. Hygromycin (200 $\mu$g/ml) (Calbiochem, La Jolla, Calif.) was used to select for transfected cells and expression of HB5 or YZ 1 was evaluated using flow cytometry.

Antibodies: The antiCR2 mAb HB5 (mouse IgG2a) (American Type Culture Collection, Rockville, Md.), specific for SCR3 and 4 of human CR2, was used to detect the VCP and VCP deletion mutants. The anti-CRI mAb YZ-1 (mouse IgG1) has three distinct binding sites on human CR1. RPC5.4 (IgG2a) and MOPC21 (IgG1 ) are mouse mAbs used as non-specific isotype-matched controls.

were washed using FACS buffer, resuspended in 50 $\mu$l of fluorescein-conjugated antibody (1 $\mu$g/ml), incubated for 30 minutes on ice, washed in FACS buffer, resuspended in 300–500 $\mu$ul of FACS buffer, and analyzed using a Becton-Dickenson FACScan instrument. Wild type cells served as a negative control cell.

Assay for VCP function: Stably transfected K562 cells expressing either CR1, VCP, or one of the 5 deletion mutants were washed in FACS buffer, incubated for 30 minutes with either PBS or C3b dimers 10 $\mu$/ml in PBS, washed with FACS buffer and incubated with fluorescein-conjugated goat anti-human C3. Specific binding was determined by flow cytometry.

Functional Sorting of L Cells: L cells grown in 96-well plates to 50% confluence were exposed to anti-L cell/NIH3T3 cell anti-bodies at 1:25 in Hank's Balanced Salt Solution (Life Technologies) at 4° C. for 30 minutes. The wells were washed once with Hank's Solution and incubated with either heat inactivated (30 minutes, 56° C.) or normal rabbit complement-DR Type (Pel-Freez, Brown Deer, Wis.) at 1:4 dilution. After 3 and 7 consecutive exposures over 3 and 6 week periods, respectively, the expression levels of VCP-CR2 were determined by flow cytometry.

Complement-mediated Killing of L Cells: L cells grown to 50–80% confluence in 96 well plates were washed twice with Hank's solution, incubated at 4° C. for 30 minutes with 1:25 dilution of anti-L cell/NIH3T3 cell antiserum, washed once with Hank's solution and incubated for 45–60 minutes at different dilutions in Hank's Solution of heat inactivated (30 minutes, 56° C.) or normal rabbit complement in triplicate. The solution in each well along with the adherent cells were lifted with PE buffer, harvested, and resuspended in 250 $\mu$l of propidium iodide (PI; 0.5 $\mu$g/ml in PBS) and 50 $\mu$l of FACS buffer were added and killing was immediately estimated using a FACScan. The percent of cells that had incorporated PI was determined by analyzing 1000 events per sample with a FACScan. The $CH_{50}$ was calculated using the equation: log(y/1−y) versus log serum dilution. y=(sample lysis−control lysis)/100% lysis−control lysis). Control lysis=lysis at the same dilution of heat inactivated serum. Maximum cytotoxicity=100%. The assays were performed in triplicate.

Killing Curve and staining of HB5: L cells bearing VCP-CR2 (L cells.RelVCP1234) were grown to 50–80% confluency in 12 well plates, washed twice with Hank's Solution, incubated at 4° C. for 30 minutes with 1:25 dilution of anti-L cell/NH3T3 cell anti-serum, washed once with Hank's solution and incubated for 45–60 minutes with different dilutions of complement or heat inactivated complement in HBSS. The supernatant and adherent cells from each well were lifted with PE buffer, pelleted, split into two tubes, and indirectly stained with mAb HB5 or isotype matched control antibody, followed by DTAF goat-anti mouse IgG. Immediately prior to analyzing the samples by flow cytometry, 50 µl of PI was added to the 250 µl sample. Two color (DTAF and PI) flow cytometric analysis of 1,000 events were recorded per sample. A four quadrant analysis was used to identify the percentage of cells that were alive and HB5-positive, as compared with HB5-negative.

Figure 7A:
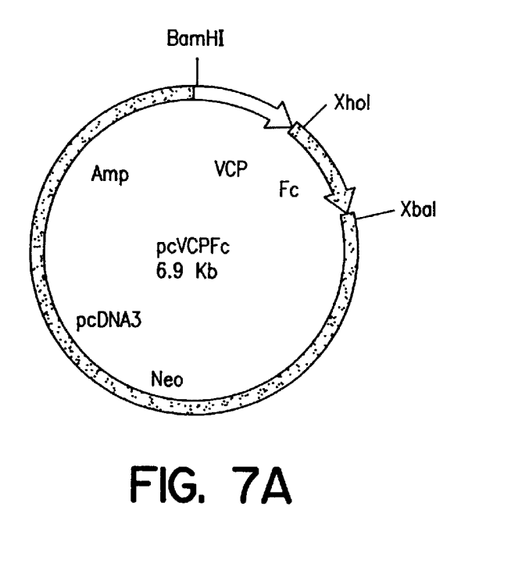
FIG. 7A is a map of the pcVCPFc plasmid encoding the VCPFc fusion protein. The sequences of SCR-1 through −4 of VCP and mouse Fc were combined and inserted into pcDNA3 expression vector.
Figure 7B:
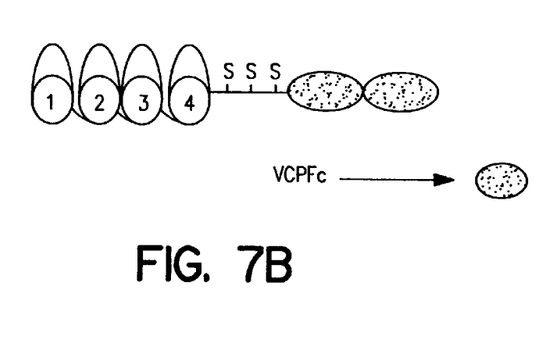
FIG. 7B is a schematic diagram of the 4 SCRs of VCP attached to the hinge region of mouse Fc (IgG2a).

Creation of pcVCPFc and production of VCPFc: Plasmid pApHyg is a eukaryotic expression vector created by cloning the 3.9 kb BamHI-PvuI restriction fragment encoding Hygromycin B resistance from plasmid pHYG into plasmid pAprM8, encoding ampicillin resistance. Plasmid pcisCD19Fc encodes a fusion protein that consists of the extracellular domain of human CD19 fused to the Fc domain of mouse IgG2a. A fragment encoding the Fc domain was removed from pcisCD 1 9Fc by restriction with XhoI and XbaI, a HindIII-XhoI fragment encoding VCP was removed from pRelVCP1234, and the two fragments were ligated with ApHyg that had been restricted by HindIII and XbaI to create pApHygVCP. A BamHI-XbaI fragment encoding the VCPFc fusion was removed and ligated to BamHI-XbaI-digested pcDNA3 (Invitrogen; San Diego, Calif.), creating pcVCPFc (FIGS. 7A and 7B).

pcVCPFc was grown in GM48 bacteria and purified with a Qiagen plasmid prep kit (Qiagen, Chatsworth, Calif.) 293T cells were transiently transfected using a $CaPO_4$ technique (adapted from Current Protocols) and induced with butyric acid 12–24 hours after transfection. Culture supernatant was harvested 48 hours after transfection and immunoglobulin fraction precipitated at 4° C. for 8–12 hours using sepharose CL-4B protein A beads (Pharmacia, Upsala, Sweden.) Beads were collected by centrfiigation and washed extensively with PBS. VCP-Fc was eluted with citrate pH 3.0, neutralized with Tris pH 9.0, dialyzed against PBS and concentrated in a centricon-30 concentrator (Amicon, Beverly, Mass.).

Figure 7C:
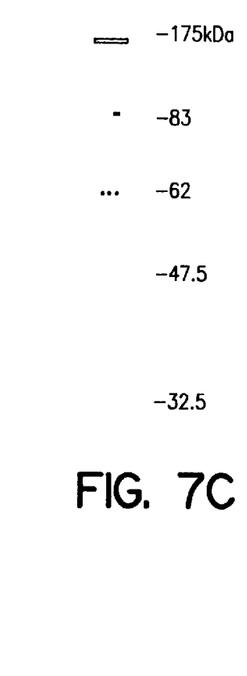
FIG. 7C is an SDS-polyacrylamide reducing gel of purified VCPFc demonstrates the correct molecular size.

VCP-Fc size and purity were evaluated by SDS-PAGE using the Laemmli discontinuous buffer system: VCP-Fc migrated at 115 kDa through a non-reducing 6% gel, and at 55 kDa in the presence of DTT through a 10% gel (FIG. 7C).

Erythrocyte Antibody Complement Intermediates:

Preparation of control EA: Prewarmed and previously washed EAs were combined with 125 µl of Gelatin Veronal Buffer (GVB) and warmed to 37° C. for 45 minutes, washed 3 times in ice-cold GVB, and resuspended in 500,ul of GVB.

Preparation of EAC4biC3b: Antibody sensitized sheep erythrocytes (EA) (Sigma, St. Louis, Mo.) were washed with GVB with Ca++ and Mg++ (GVB) (Sigma) and adjusted to $1×10^8$/ml. Pre-warmed 300 µl of EA and 50 µl C5-depleted human serum (C5DS) (Quidel) diluted in GVB were combined, warmed at 37° C. for 45 minutes, washed 3 times in ice-cold GVB and resuspended in 400 µl of GVB.

Preparation of EAC4bC3b (with very low expression levels of iC3b): 300 µl of EA and 50 µl C3-depleted human serum (C3DS)(Quidel) diluted in GVB were combined, warmed to 30° C. for 10 minutes. 8 µl of anti-Factor I#1 (Anti-D (Quidel was added to the EAs-C3DS combinations). After 5–10 minutes, the EAs were washed with ice-cold GVB. Human C3 (25 ug) (Quidel) diluted 1:4 in GVB and 9 µl of anti-I were combined and warmed to 30° C. for 40 minutes. The cells were washed three times and resuspended in 500 µl of GVB. All intermediates were evaluated by flow cytometry for expression of C4d, iC3b, and C3dg.

Rosette Assays: L cell transfectants or control cells were lifted from 70–80% confluent 100 mm dishes with PE buffer, washed with ice cold GVB and resuspended in approximately 300–400 µl of GVB. Equal volumes of fresh EAC intermediates and L cells were combined at room temperature for approximately one hour. 20 µl of the EAC intermediate/L cell suspensions were placed on a covered microscope slide. At least 200 cells were counted per slide and the mean percentage of cells forming rosettes, i.e. binding three or more EAC, was determined. For inhibition studies, prior to combining the EAC with the L cells, the fresh EAC intermediates were combined with 80–100 µg/ml of VCPFc, sCR1 or control protein (either CTLA4Ig or CD44Fc on ice for 30 minutes.

Discussion of Results

1. VCP Requires Four SCRs to bind C3b

Figure 1:
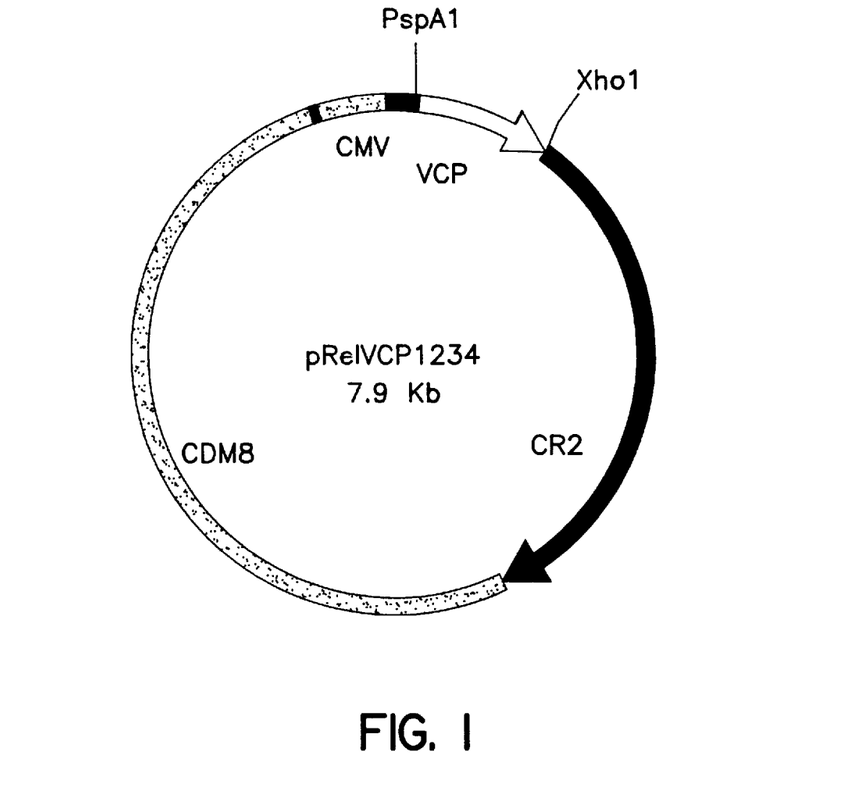
Figure 2A:
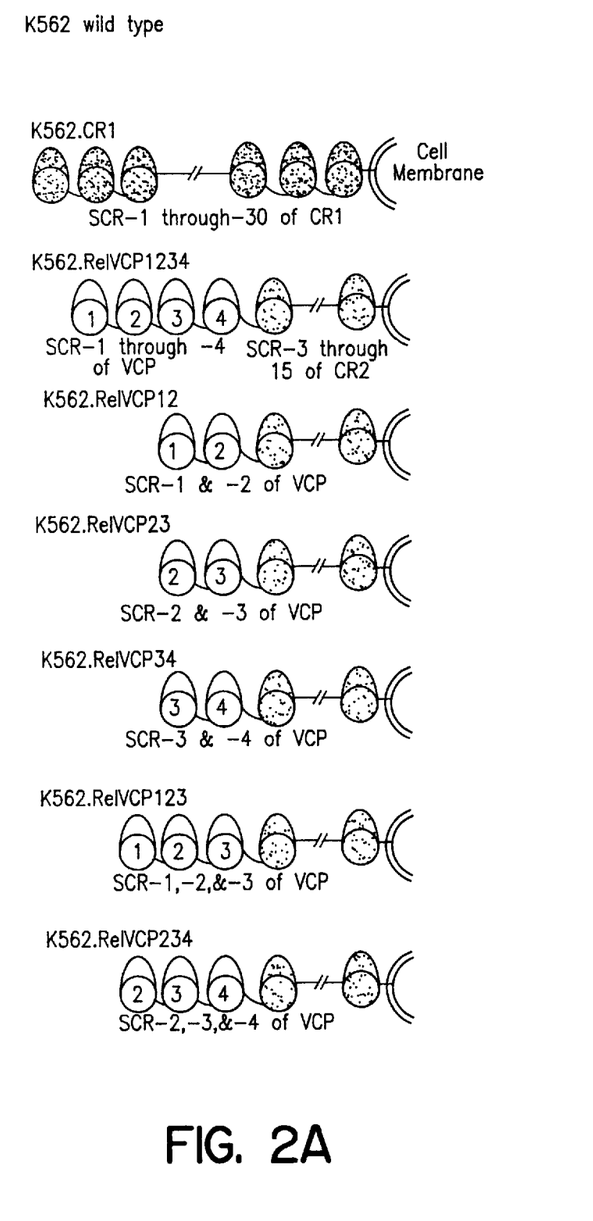
FIG. 2A is a schematic representation of the relevant SCRs in various transfected cell lines. K562.CR1 expresses human CR1 with 30 SCRS. K562.RelVCP1234 encodes the four SCRs of VCP in place of SCR-1 and −2 of CR2. The remaining five deletion mutants have the relevant SCRs of VCP depicted in white in place of SCR-1 and −2 of CR2.
Figure 2B:
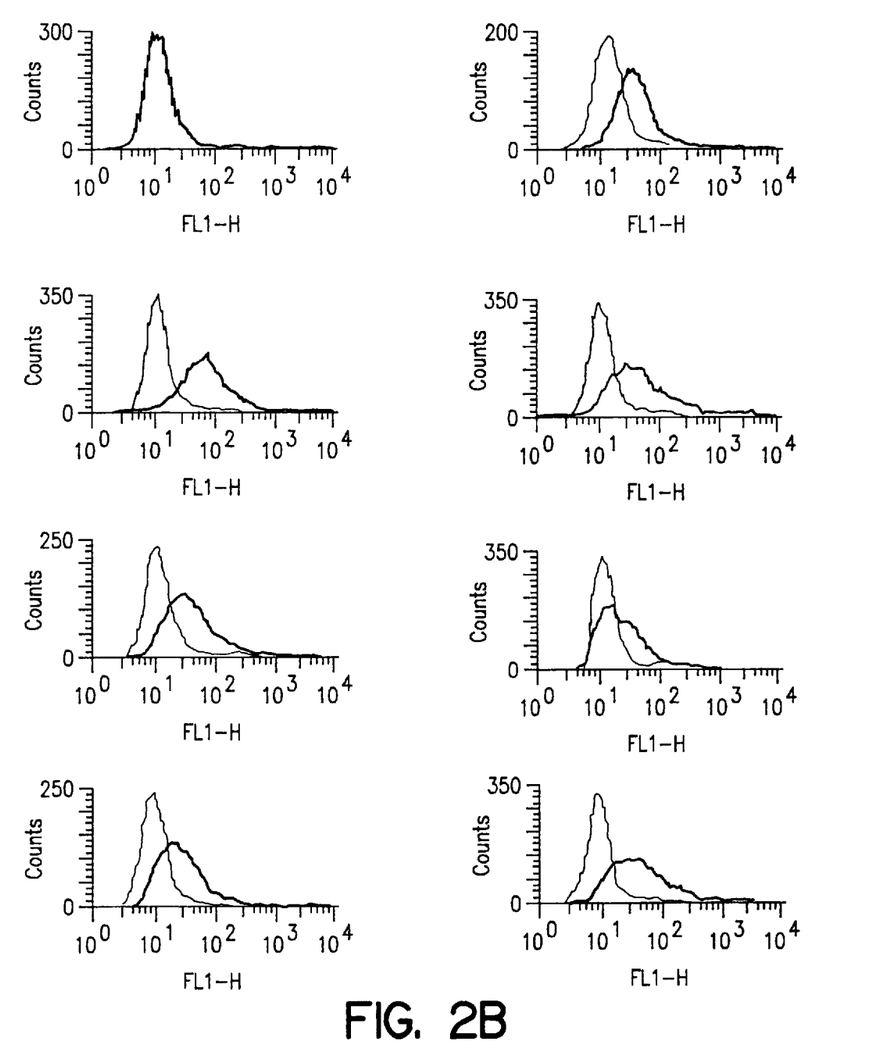
FIG. 2B shows the results of flow cytometric analysis of K562 cells stably expressing CR1, VCP or one of five deletion mutants that have been indirectly stained with control antibody (thin solid line) or YZ1 anti-CR1 (thick solid line) or HB5 anti-SCR-3 or 4 of CR2 (thick solid line) followed by fluorescein-conjugated goat anti-mouse Ig.
Figure 2C:
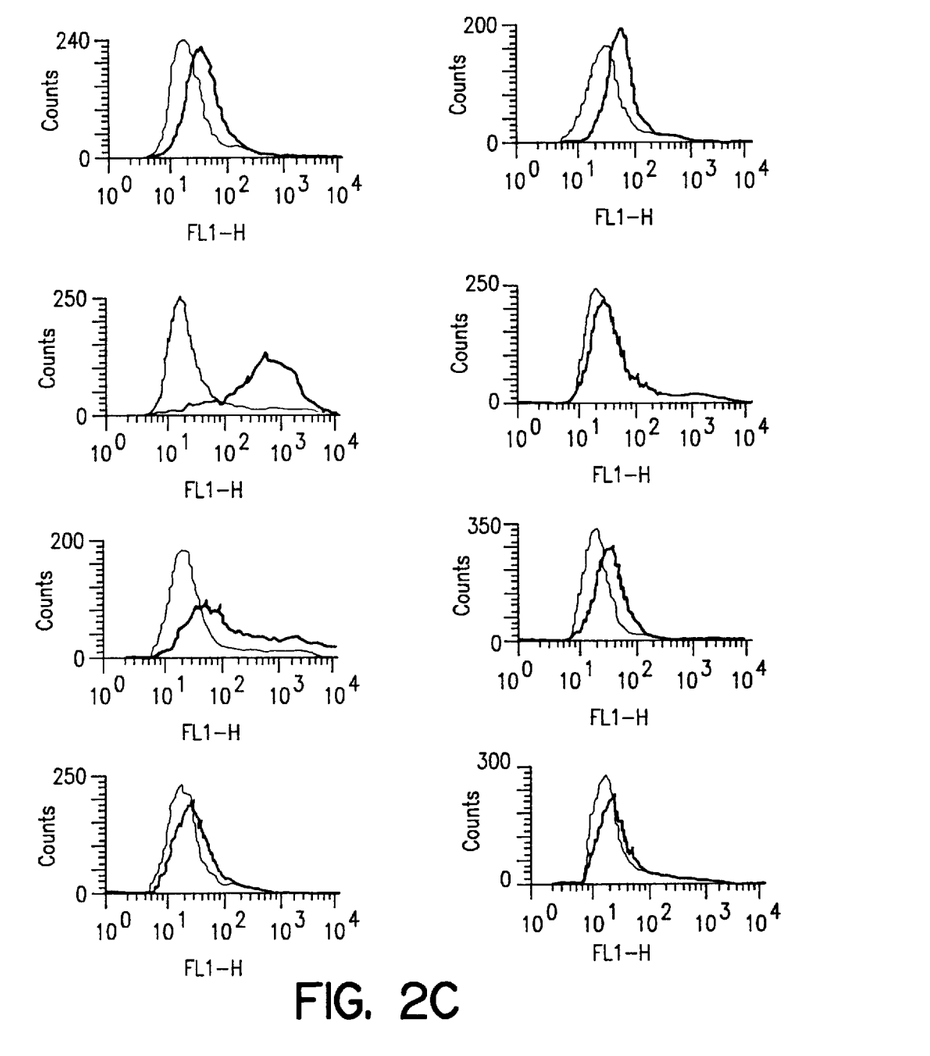
FIG. 2C shows the results of flow cytometric analysis of the C3b binding-capacity of K562 cells stably expressing CR1, VCP, or one of five deletion mutants. No ligand (thin solid line) or C3b-dimers (thin solid line) were stained using a fluorescein-conjugated goat anti-human C3 Ig.

By constructing a panel of recombinant VCP mutants, we have mapped the functional domain of VCP and shown that this viral protein can protect cells from complement-mediated lysis. All four short consensus regions (SCRs) of VCP are needed for full VCP function. The panel of recombinant VCP proteins were produced as membrane-bound receptors. In these recombinant proteins, SCR-1 and SCR-2 of human CR2 were replaced either by the four SCRs that comprise wild type VCP (VCP-CR2) or with one of five deletion mutants encoding two (VCP12-CR2; VCP23-CR2; VCP34-CR2) or three (VCP123-CR2; VCP234-CR2) contiguous SCRs of VCP, as shown in FIGS. 1 and 2A. These expression vectors, and an analogous construct encoding wild type human CR1, were transfected into human K562 cells. Stable cell lines were characterized by flow cytometric analysis for expression of the transfected proteins. As shown in FIG. 2B, we generated a panel of K562 cell lines stably expressing wild type human CR1, the chimera VCP-CR2, or one of the deletion mutants. These seven lines were compared with wild type K562 cells for the capacity to bind C3b by flow cytometric analysis, as shown in FIG. 2C.

Several conclusions can be drawn from these data. First, these data show that cells expressing VCP-CR2 were able to bind C3b, as demonstrated by a shift in the histogram that represents specific staining as compared with staining of wild type cells. Second, none of the deletion mutants demonstrated specific binding of C3b as compared with wild type cells. Third, when compared with K562.CR1 cells, there was a much broader range of specific fluorescence observed with VCP-CR2 cells than with CR1. This suggests that CR1 may have a greater avidity for C3b than does VCP, perhaps due to the presence of three ligand binding domains within a single CR1 molecule. In sum, these data show that VCP, when anchored to the plasma membrane (by CR2), binds C3b; all four SCRs are required for binding.

Figure 3A:
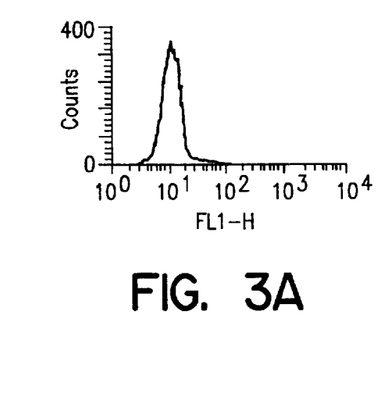
Figure 3B:
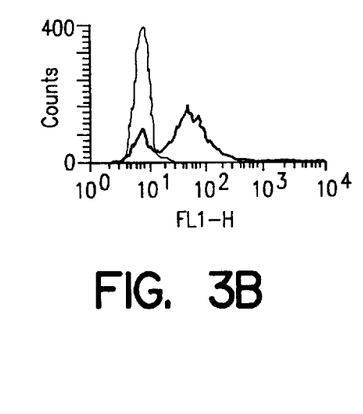
Figure 3C:
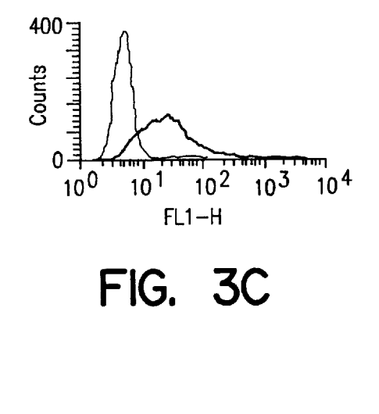
Figures 4A, 4B:
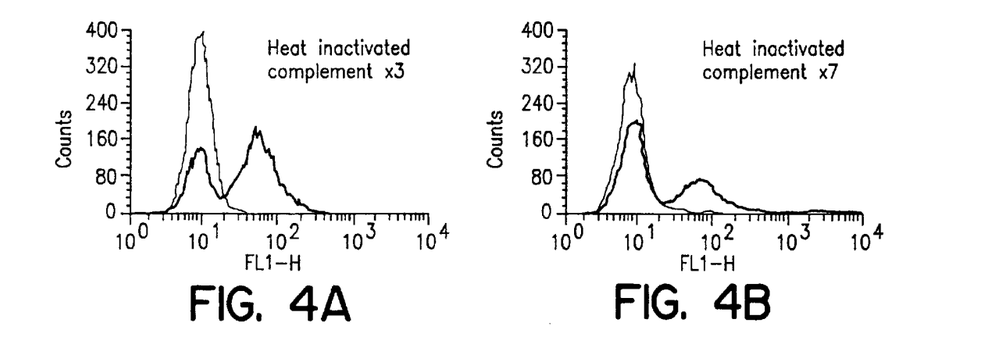
FIGS. 4A–4D represent functional sorting of L cells.RelVCP1234 using flow cytometric analysis of HB5 expression levels after repeated exposures to heat inactivated or normal rabbit complement.
Figures 4C, 4D:
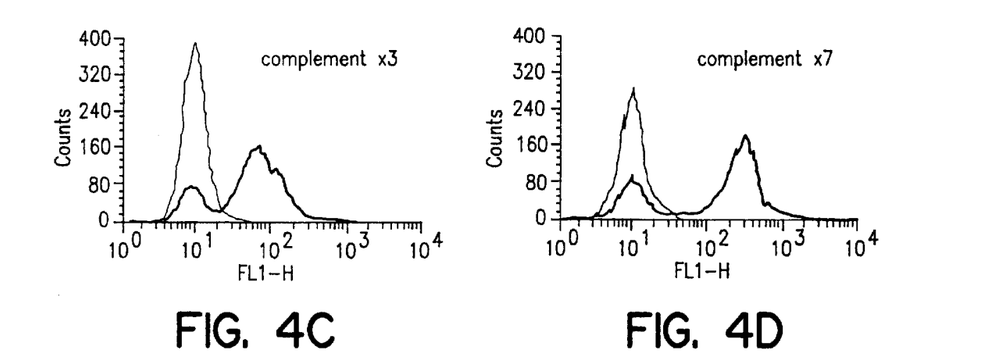

2. Expression of VCP on Cell Membranes Protects Cells from Complement-Mediated Lysis To produce mammalian cells expressing either VCP or CR1, mouse L cells were transfected with plasmids encoding either VCP-CR2 or human CR1, and transfectant were selected for antibiotic resistance. Populations of L cells bearing CR1 or VCP-CR2 were identified by the anti-CR1 and anti-CR2 mAbs YZ-1 and HB-5, respectively. As shown in FIG. 3C, transfection and antibiotic selection generated a population of cells, all of which expressed human CR1. In contrast, a bimodal histogram was obtained for L cells bearing VCP-CR2 (FIG. 3B), indicating that VCP-CR2-positive cells as well as VCP-negative cells had proliferated when selected with G418. A histogram obtained for wild type cells is provided in FIG. 3A.

Cells expressing the chimeric receptor VCP-CR2 were recovered by utilizing the ability of VCP to protect cells from complement-mediated lysis. A bimodal pattern of expression of VCP-CR2 on L cells enabled us to "functionally sort" for those L cells bearing the highest levels of VCP-CR2 simply by repeatedly exposing the cells to rabbit serum as a source of complement. As shown in FIGS. 4A–4D, repeated incubations of L.VCP-CR2 transfectants with anti-L cell antiserum followed by heat inactivated serum actually resulted in a net loss of receptor expression. In contrast, repeated incubations of L.VCP-CR2 cells with anti-L cell antiserum, followed by fresh rabbit serum as a source of complement, resulted in selection of cells that expressed VCP-CR2. After three sequential incubations, the ability to functionally select for cells bearing VCP-CR2 was apparent, and this ability was most pronounced after seven sequential incubations with complement. Following this selection process, we observed an increase in the percentage of cells in the culture that were VCP-CR2-positive. This effect is reflected in relative changes in the amplitudes of the two histograms shown in FIGS. 4A versus FIG. 4C and FIG. 4B versus FIG. 4D. These data show that one can successfully select for cells bearing the highest levels of VCP-CR2 through complement-mediated lysis of transfectants previously selected for antibiotic resistance alone.

Figure 5:
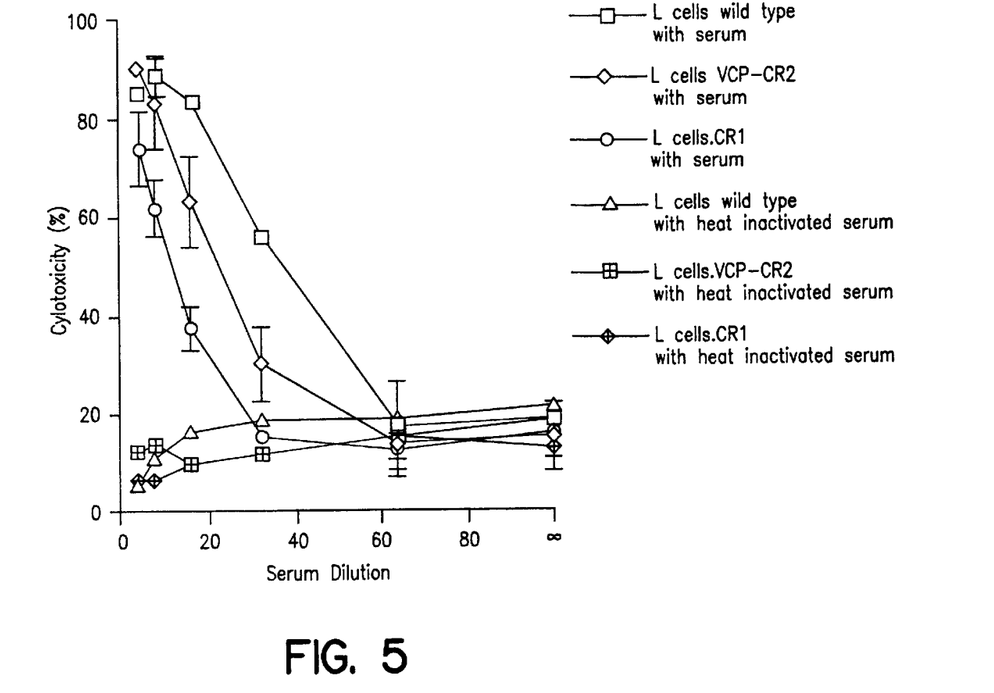
FIG. 5 illustrates the percent of L cells transfectants killed following exposure to different dilutions of heat inactivated or normal rabbit complement. L cells.wild type, RelVCP1234, and CR1 were exposed to different concentration of complement or heat inactivated complement. The percent of cells killed were assessed using flow cytometric analysis for propidium iodide inclusion. This graph translated to $CH_{50}$ of 30, 19, and 11 for L cells.wild type, L cells.CR1 and L cells.RelVCP1234, respectively, when using the equation log (y/1−y) versus serum dilution. y=(sample lysis—control lysis)/(100% lysis-control lysis). Control lysis=lysis at the same dilution of heat inactivated serum. Maximum killing=100%.

As is illustrated in FIG. 5, membrane-bound VCP (VCP-CR2) inhibits complement-mediated cell lysis. L cells bearing either CR1 or VCP-CR2 were incubated with anti-L cell antiserum followed by serial dilutions of rabbit serum as a source of complement or heat inactivated serum. Specific complement-mediated cell lysis was observed at serum dilutions of 1:32 or less, and lysis was inhibited by surface expression of either VCP-CR2 or CR1. More cells bearing CR1 survived at each serum dilution compared with those expressing VCP-CR2. This difference, however, is due to the bimodal distribution of the population of L.VCP-CR2 cells, where a subset of the cells lacked surface expression of VCP-CR2.

Figure 6A:
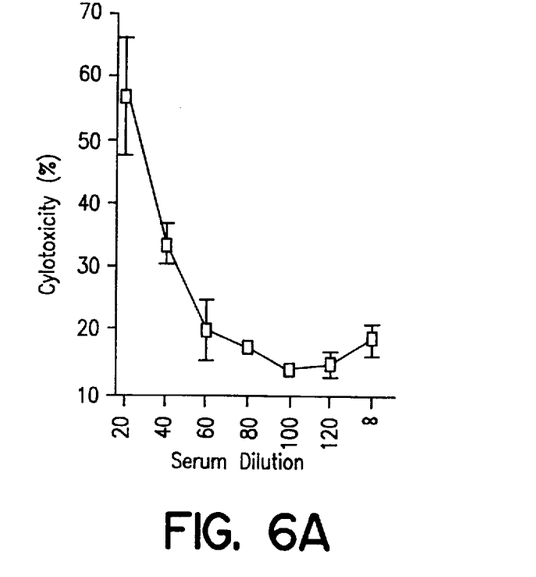
FIGS. 6A–6B illustrate the percent killing of L cells.RelVCP1234 treated with different dilutions of normal rabbit complement and ratio of live cells expressing HB5 versus those live cells not expressing HB5. L cells.RelVCP1234 were exposed to different concentrations of complement. The percent of cells killed (FIG. 6A) and staining positive for HB5 (FIG. 6B) was assessed using flow cytometric analysis with double staining of the L cells.RelVCP 1234 for both propidium iodide and HB5 expression.
Figure 6B:
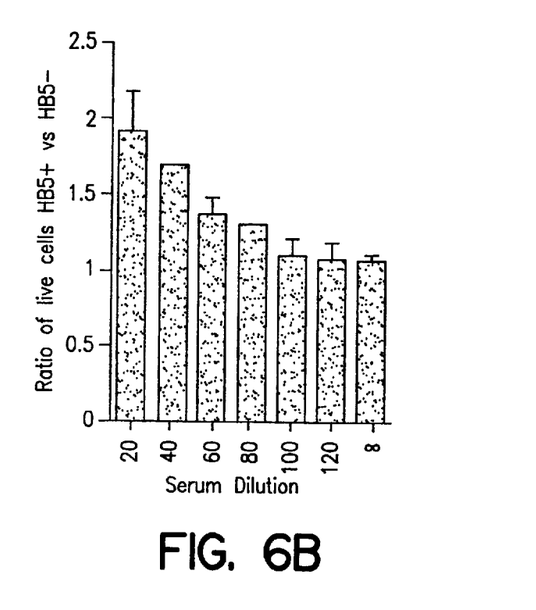

To show that cells expressing VCP were protected from complement-mediated lysis, in contrast to cells that did not express VCP, we determined the percentage of VCP-CR2-positive cells that survived complement attack. L.VCP-CR2 cells were incubated in anti-L cell antiserum followed by serial dilutions of fresh rabbit serum and assayed simultaneously for cell death as well as expression of VCP-CR2 on surviving cells by two color fluorescence flow cytometry using propidium iodide and the anti-CR2 mAb HB5, respectively. Complement-mediated cytolysis was observed as serum dilutions of 1:80 and less (FIGS. 6A and 6B). At more dilute serum concentrations, no specific cytotoxicity was observed and the ratio of HB5+ to HB5-cells following incubation was approximately equal. However, when samples of L.VCP-CR2 cells were incubated in rabbit serum at dilutions ranging from 1:20 to 1:80, a greater proportion of surviving cells were HB5+ as compared with HB5−; the number of VCP-positive cells is nearly twice that of VCP-negative cells. This ratio increased progressively with increasing serum concentration and consequently more effective cytotoxicity. Thus, cells expressing VCP were protected from complement-mediated lysis, whereas cells that did not express VCP were not protected.

3. VCP Binds C3b but not C3bi

VCP-CR2 was compared with CR1 for the ability to bind C3bi in a rosette assay using L cells bearing either CR1 or VCP-CR2 and erythrocyte intermediates coated with C3b or C3bi. EAC3bi were created by incubating antibody-sensitized erythrocytes (EA) in C5-deficient serum. EAC3b were created by sequential incubation of EA with C3-deficient serum, followed by purified C3 in the presence of anti-factor I, which inhibits conversion of C3b to C3bi. Erythrocyte intermediates were assayed for deposition and processing of C3 by indirect immunofluorescence and flow cytometric analysis. These assays were based on the capacity of mAb anti-C3d to recognize both C3b and C3bi, whereas the mAb anti-C3bi is specific for a neoepitope on C3bi and, therefore, does not recognize C3b. EA are not recognized by either mAb, as shown in FIGS. 8A–8D. EAC3b react strongly with mAb anti-C3d, but only weakly with mAb anti-C3bi, indicating that most of the C3 is in the form of C3b. EAC3bi react strongly with mAb anti-C3d, and almost as strongly with anti-C3bi, which is specific for the fragment. These data indicate that the EAC3b bear mostly C3b, with a low level of C3bi, whereas EAC3bi bear mostly C3bi.

Figure 8A:
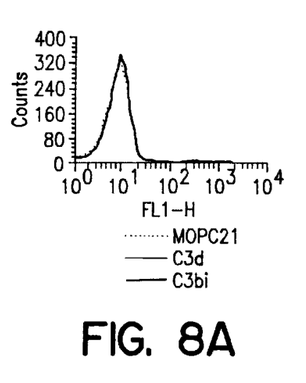
FIGS. 8A–8E provide a functional comparison of CR1 and VCP. EA (FIG. 8A) and EA bearing C3b (FIG. 8B) or C3bi (FIG. 8C) were characterized for the capacity to form rosettes with wild type L cells and with L cells expressing CR1 or VCP-CR2 (FIG. 8D). Characterization of erythrocyte intermediates (FIGS. 8A–8C) was performed by indirect immunofluorescence and flow cytometric analysis using monoclonal antibodies anti-C3d, anti-C3bi, and an isotype matched control. Anti-C3d recognizes both C3b and C3bi. Anti-C3bi is specific for a neoepitope on the C3bi fragment. Rosette formation was determined by coincubation of erythrocyte intermediates with wild type L cells, L cells bearing CR1, or L cells bearing VCP-CR2 for 45 minutes. At least 200 L cells were counted in each sample. A rosette was defined as an L cell bearing at least three erythrocytes. L cells bearing CR1 form rosettes with EAC3b and EAC3bi, whereas L cells bearing VCP-CR2 form rosettes only with EAC3b (FIG. 8D). VCPFc and soluble CR1 (100 μg/ml) were compared for the capacity to block rosettes formed by L cells bearing VCP-CR2 and EAC3b (FIG. 8E). CTLA4Ig and CD44Fc served as negative controls.
Figure 8B:
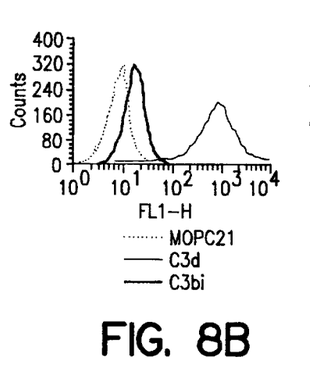
Figure 8C:
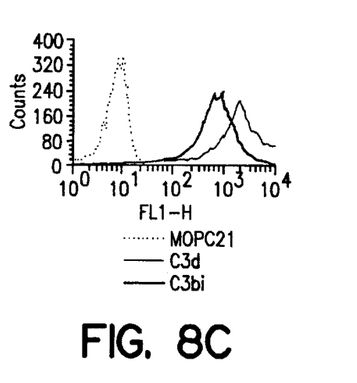
Figure 8D:
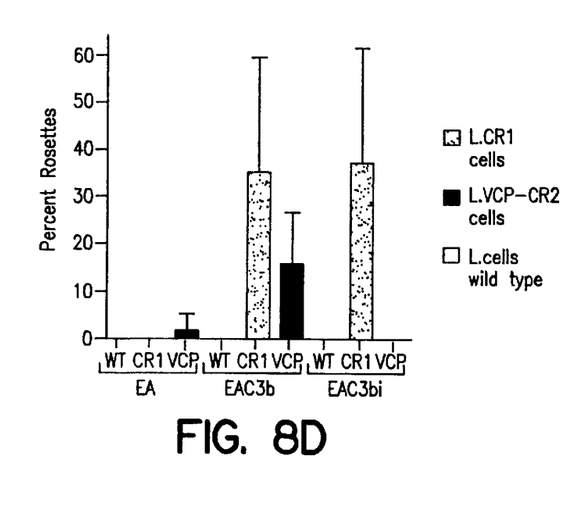

These EA, EAC3b, and EAC3bi were compared for their ability to form rosettes when mixed with L.WT, L.CR1, or L.VCP-CR2 cells, respectively (FIG. 8D). Rosettes formed specifically between L.CR1 and EAC3b (35%) and to an equal degree between L.CR1 and EAC3bi (37%). L cells expressing VCP-CR2 effectively formed rosettes with EAC3b (15%). Surprisingly, no rosettes were observed between L.VCP-CR2 and EAC3bi. This difference in the ability to bind C3bi is the first qualitative finctional distinction made between VCP and CR1.

Having recognized the ability of membrane-bound VCP to inhibit complement-mediated cell lysis, the present inventors have also presumed a transgenic mammal to be within the invention. The transgenic mammals of the invention are useful donors in methods of xenograft transplantation. In such a transgenic mammal, the genome of the mammal is engineered to encode a fusion protein in which SCRs 1–4 of VCP are fused to a transmembrane anchoring domain (e.g., CR2). Organs from these transgenic mammals can be used to inhibit hyperacute rejection of xenografts. Organs obtained from these transgenic mammals offer the advantage that the membrane-bound VCP protein expressed on the organs provides local anti-complement activity, as opposed to systemically inhibiting complement.

Figure 8E:
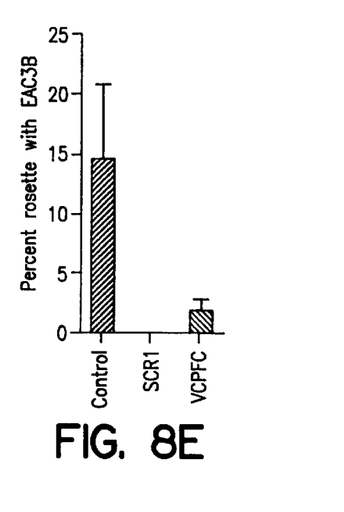

4. VCPFc is a Soluble and Specific Inhibitor of Complement-Mediated Cell Lysis The recombinant, soluble form of VCP was created and shown to inhibit C3b-receptor interactions. The genetic construct, pcVCPFc, encodes full-length VCP fused to the Fc domain of mouse IgG2a; this construct was transfected transiently into 293T cells. The VCPFc polypeptide was purified from these cells by protein A chromatography, and characterized by SDS polyacrylarnide gel electrophoresis (FIGS. 8A–8C). A single protein band, having an estimated molecular weight of 55 kD, was observed. VCPFc was compared with sCRI for the ability to inhibit rosette formation between L.VCP-CR2 and EAC3b (FIG. 8E). Control proteins CD44Fc and CTLA4Ig had no effect on the percent of rosettes formed (~15%), as compared with buffer alone. However, both VCPFc (100 μg/ml) and sCRI (100 μg/ml) inhibited the percentage of L.VCP-CR2 cells forming rosettes with EAC3b by 90% and 100%, respectively.

The VCPFc fusion protein can readily be prepared as a pharmaceutical formulation by admixture of the fusion protein with a pharmaceutically acceptable excipient, such as saline, water, and the like. Typically, the concentration of VCPFc protein in the pharmaceutical formulation is 1 to 500 mg/ml, and preferably 1 to 10 mg/ml. The VCPFc and/or immunosuppressive agent is administered to a mammal afflicted with a complement-mediated disorder, an organ donor or an organ recipient by any suitable means, including parenteral, subcutaneous, intrapulmonary, and intranasal administration, and if desired for local treatment, intralesional administration (including perfusing or otherwise contacting a graft with VCPFc or an immunosuppressive agent prior to transplantation). Parenteral infusions include intramuscular, intravenous, intraarterial, or intraperitoneal administration. In addition, the immunosuppressive agent is suitably administered by pulse infusion, particularly with declining doses of the immunosuppressive agent. Preferably, the dosing is given by injections, most preferably intravenous or subcutaneous injections, depending in part on whether the administration is brief or chronic. Where an organ to be transplanted is treated with VCPFc, any of the commonly-known methods for perfusing liquids through organs are suitable for use. Other appropriate means for treating the transplanted organ include using genetic engineering methods to express VCP in the organ (e.g., by infecting cells of the organ with a virus (e.g., an adenovirus) that expresses a VCP or VCPFc gene). In practicing the invention, the VCPFc is administered to the donor, in an amount sufficient to decrease complement activity to 50% or less, preferably to 10% or less, of normal. Typically, VCPFc is administered at a dosage of 1–1,000 mg/kg, preferably 1–50 mg/kg. If desired, administration of VCPFc to the donor, organ, and/or afflicted mammal can be repeated in order to optimize inhibition of complement.

The VCPFc protein of the invention can be used generally for inhibiting a complement-mediated tissue damage in a mammal. In particular, the VCPFc protein is useful in xenotransplantation methods and in methods for treating inflammation. This fusion protein is particularly useful in treating neurological inflammation, including spinal cord injury. In addition, injection of VCPFc into synovial cells of arthritic joints provides a method for treating arthritis. VCPFc can also be used to reduce ischemia-induced reperfusion injury in myocardial and skeletal muscle and in intestinal and pulmonary tissues. The VCPFc chimera is also useful for decreasing the morphologic and functional consequences of complement-mediated glomerulonephritis and encephalomyelitis. In addition, the VCPFc chimera can be used to inhibit the reversed passive Arthus reaction, and decrease thermal injury-induced damage. Both the membrane-bound VCP and the VCPFc chimera offer the advantage of not binding iC3b. Other complement control proteins bind iC3b, which allows attachment of antibody complexes. Because the attachment of such antibody complexes is undesirable, the use of VCP is favorable to the use of other complement control proteins, such as CR1.

Although the invention has been described with reference to the presently preferred embodiment, it should be understood that various modifications can be made without departing from the spirit of the invention. Accordingly, the invention is limited only by the following claims.

What is claimed is:

1. A cell expressing at its surface (i) a transmembrane anchoring domain, fused to (ii) a polypeptide that comprises a portion of a vaccinia virus complement control protein that binds complement components C4b and C3b, but not iC3b rosettes.

2. The cell of claim 1, wherein the polypeptide comprises short consensus regions 1 through 4 of VCP.

3. The cell of claim 1, wherein the transmembrane anchoring domain comprises short consensus regions 3 through 15 of human complement receptor 2 protein.

4. A nucleic acid construct encoding (i) a transmembrane anchoring domain, fused to (ii) a polypeptide that comprises a portion of a vaccinia virus complement control protein that binds complement components C4b and C3b, but not iC3b rosettes.

5. The nucleic acid construct of claim 4, wherein the transmembrane anchoring domain comprises short consensus regions 3 through 15 of human complement receptor 2 protein.

6. The nucleic acid construct of claim 4, wherein the polypeptide comprises short consensus regions 1 through 4 of VCP.

7. A method for producing a polypeptide having (i) a transmembrane anchoring domain, fused to (ii) a polypeptide that comprises a portion of a vaccinia virus complement control protein that binds complement components C4b and C3b, but not iC3b rosettes, comprising introducing a nucleic acid construct encoding the polypeptide into a suitable host cell, under conditions that allow expression of the nucleic acid construct, thereby producing the polypeptide.

* * * * *